United States Patent [19]

Scott

[11] Patent Number: 4,886,258

[45] Date of Patent: Dec. 12, 1989

[54] WELL LEG OPERATIVE SUPPORT

[76] Inventor: James W. Scott, P.O. Box 7630, Tifton, Ga. 31794

[21] Appl. No.: 235,621

[22] Filed: Aug. 24, 1988

[51] Int. Cl.[4] ........................ A61G 13/00; A61F 5/00; A61F 5/37

[52] U.S. Cl. ................................ 269/328; 128/80 R; 128/80 F; 128/83; 128/87 R

[58] Field of Search ...................... 5/443, 60; 269/328, 269/322; 128/80 R, 845, 882, 87 R, 80 F, 589, 600, 606, 623, 80 H, 83

[56] References Cited

U.S. PATENT DOCUMENTS

| | | | |
|---|---|---|---|
| 1,516,795 | 1/1924 | Schwarting | 248/118 |
| 2,057,992 | 10/1936 | Wiruth | 269/328 |
| 2,067,891 | 1/1937 | Comper | 269/328 |
| 2,257,491 | 9/1941 | Armstrong | 269/322 |
| 2,470,026 | 5/1949 | Freund . | |
| 3,606,884 | 9/1971 | Peter . | |
| 4,166,460 | 9/1979 | Applegate | 128/80 H |
| 4,186,738 | 2/1980 | Schleicher et al. | 128/80 R |
| 4,407,277 | 10/1983 | Ellison | 128/82 |
| 4,426,071 | 1/1984 | Kleustad | 269/328 |
| 4,443,005 | 4/1984 | Sugarman | 269/328 |
| 4,564,164 | 1/1986 | Allen | 269/322 |
| 4,573,482 | 3/1986 | Williams, Jr. | 128/882 |
| 4,615,516 | 10/1986 | Stulberg et al. | 128/80 R |
| 4,809,687 | 3/1989 | Allen | 269/328 |

OTHER PUBLICATIONS

Allen/Edgewater Medical Systems, Inc. Product Brochure at least as early as Jun. 9, 1987.

Olis-Schanlan A2148J Date prior to Aug. 24, 1987.

*Primary Examiner*—Alexander Grosz

*Attorney, Agent, or Firm*—Bradford E. Kile

[57] ABSTRACT

A well leg operative support for use during an arthroscopic and/or incision surgical procedure including a generally L-shaped bar having a first leg and a shorter second leg. The first leg is releasably connected to an operating table and the short leg is bent at a right angle with respect to the first leg and extends beneath a generally L-shaped foot bracket of the well leg operative support. The L-shaped foot bracket is adjustably connected to the short leg with at least one degree of translation adjustment and preferably two degrees of rotational adjustment. A flexible, disposable boot is releasably connected to the L-shaped foot bracket and includes a longitudinal back pocket for engagement with the long upstanding leg of the L-shaped foot bracket and a hook and/or loop patch upon the sole of the disposable boot for cooperation with a corresponding loop and/or hook patch positioned upon the base of the L-shaped foot bracket to securely but releasably connect the flexible boot to the generally L-shaped brace.

19 Claims, 3 Drawing Sheets

WELL LEG OPERATIVE SUPPORT

BACKGROUND OF THE INVENTION

This invention relates to a novel well leg support for an orthopedic procedure. More specifically, this invention relates to a well leg aperture support for an arthroscopic examination and/or surgery.

An arthroscope is an instrument that permits an orthopedist to visually examine the interior of a patient's joint. Initially arthroscopy was utilized by orthopedists as an examination tool to explore a potentially damaged knee joint. More recently the procedure has been extended to examination of other joints of the body and significantly has evolved into a very successful use during operative procedures.

One of the first arthroscopic surgical procedures involved the resection of a small necrotizinganthomatous giant cell tumor in the suprapataller recess. Following initial successes, and refinement of surgical techniques and equipment, operative arthroscopic procedures have included chondral shaving, joint debridgement, abrasion chondroplasty, lateral retinacular release and synovectomy. In the more recent past, combined procedures have been successfully performed wherein operative arthroscopy and independent incision of a knee have been combined to perform meniscal repair and ligament reconstruction.

Over the past three decades, arthroscopic techniques have evolved to the point that arthroscopy is one of the most common, surgical procedures performed by orthopedists. Particularly with respect to the more recent techniques; however, near—total circumferential access to an operative knee is required. Accordingly, it is necessary to abduct the well leg to permit unencumbered access to the joint of surgical interest.

In the past, the well leg has been allowed to drape over the end of an operating table by gravity and was held in position with elastic binding to a retaining member on the side of an operating table. Although expedient, this technique, particularly for an extended operative procedure, tended to induce hyperextension of the hip and/or lumbar region of the spine which created a potential for a femoral nerve traction injury, impaired venous outflow from the leg, pressure on the peroneal nerve below the knee and as a minimum postoperative soreness and patient discomfort.

The above noted technique of expediently isolating a well leg was improved by the use of a well leg knee support sculptured from foam rubber or a Silastic pad. These devices were designed to be positioned upon an operating table beneath a well knee to raise and abduct the well leg. Although the provision of a padded support was an enhancement with respect to dangling abduction, it is possible, particularly with respect to extended procedures for the peroneal nerve to be compressed tending to induce temporary paralysis in the non-operative limb following surgery. Still further, it is possible to encounter venous thrombosis resulting in vein occlusion and possible pulmonary emboli or clots to the lung.

The difficulties suggested in the proceeding are not intended to be exhaustive but rather are among many which may tend to reduce the effectiveness and physician satisfaction with prior well leg abduction techniques during arthroscopic examination and/or surgery. Other noteworthy problems may also exist; however, those presented above should be sufficient to demonstrate that well leg supports appearing in the past will admit to worthwhile improvement.

OBJECTS and BRIEF SUMMARY OF THE INVENTION

Objects

It is therefore a general object of the invention to provide a novel well leg operative support which will obviate or minimize difficulties of the type previously described.

It is a specific object of the invention to provide a well leg operative support which may be used to facilely abduct and elevate a well leg prior to an arthroscopic and/or incision surgery.

It is another object of the invention to provide a well leg operative support which will minimize the possibility of creating hyperextension of the hip and/or lumbar region of a patient's spine during knee and/or leg surgery.

It is still another object of the invention to provide an operative support which will minimize the possibility of compression of a well leg peroneal nerve during surgery or impedance of venous outflow from the extremity.

It is a further object of the invention to provide a well leg operative support which will minimize the possibility of venous thrombosis.

It is yet a further object of the invention to provide a well leg operative support which will minimize the possibility of a surgical error occurring in an operative theater through improper identification of the operative limb.

It is still a further object of the invention to provide a well leg operative support which may be facilely manipulated yet firm and secure in providing abducting placement of a well leg during arthroscopic and/or incision knee surgery and the like.

It is yet another object of the invention to provide a well leg operative support which is suitable to utilize conventional operating table clamps and may be easily manufactured and utilized by an orthopedic surgeon.

It is yet still another object of the invention to provide a well leg operative support which is personalized with respect to each patient with all patient contacting portions being disposable following an operative procedure.

BRIEF SUMMARY OF A PREFERRED EMBODIMENT OF THE INVENTION

A preferred embodiment of the invention which is intended to accomplish at least some of the foregoing objects includes a generally L-shaped bar operable to engage with and be support with selective rotational and axial adjustment by a conventional Clark type clamp found on most operating tables. A generally L-shaped foot bracket is attached, with one degree of translation and two directions of rotational adjustment to the base of the L-shaped bar extending beneath the foot bracket. The L-shaped foot bracket is fashioned with a hook and loop type strip on a base segment to engage with a flexible wall, disposable patient boot, having a hook and loop type sole pad. The flexible wall disposable boot includes a pair of lateral splints and is releasably connected to and supported by the L-shaped foot segment bracket by a longitudinal pocket engaging a leg portion of the L-shaped foot bracket. The flexible wall boot further includes a front seam to permit application to a patient and the boot is releasably held in position by an instep strap and a pair of circumferential leg straps.

In use the flexible boot is adjustably applied to a patient's well leg foot prior to entering an operating theater. An elastic pocket on the back of the boot is guided over an upstanding leg of the L-shaped foot bracket and the hook and loop type sole pad on the boot operably interfaces with the hook and loop type receiving pad on the foot of the L-shaped bracket. A Clark clamp on the operating room table and an adjustable clamp on the base of the L-shaped foot bracket are manipulated to raise and support a patient's well leg at approximately a forty five degree angle and flex the hip a similar degree. In addition the patient's well leg is abducted thirty degrees or so.

THE DRAWINGS

Other objects and advantages of the present invention will become apparent from the following detailed description of a preferred embodiment thereof taken in conjunction with the accompanying drawings, wherein.

DETAILED DESCRIPTION

Figure 1:
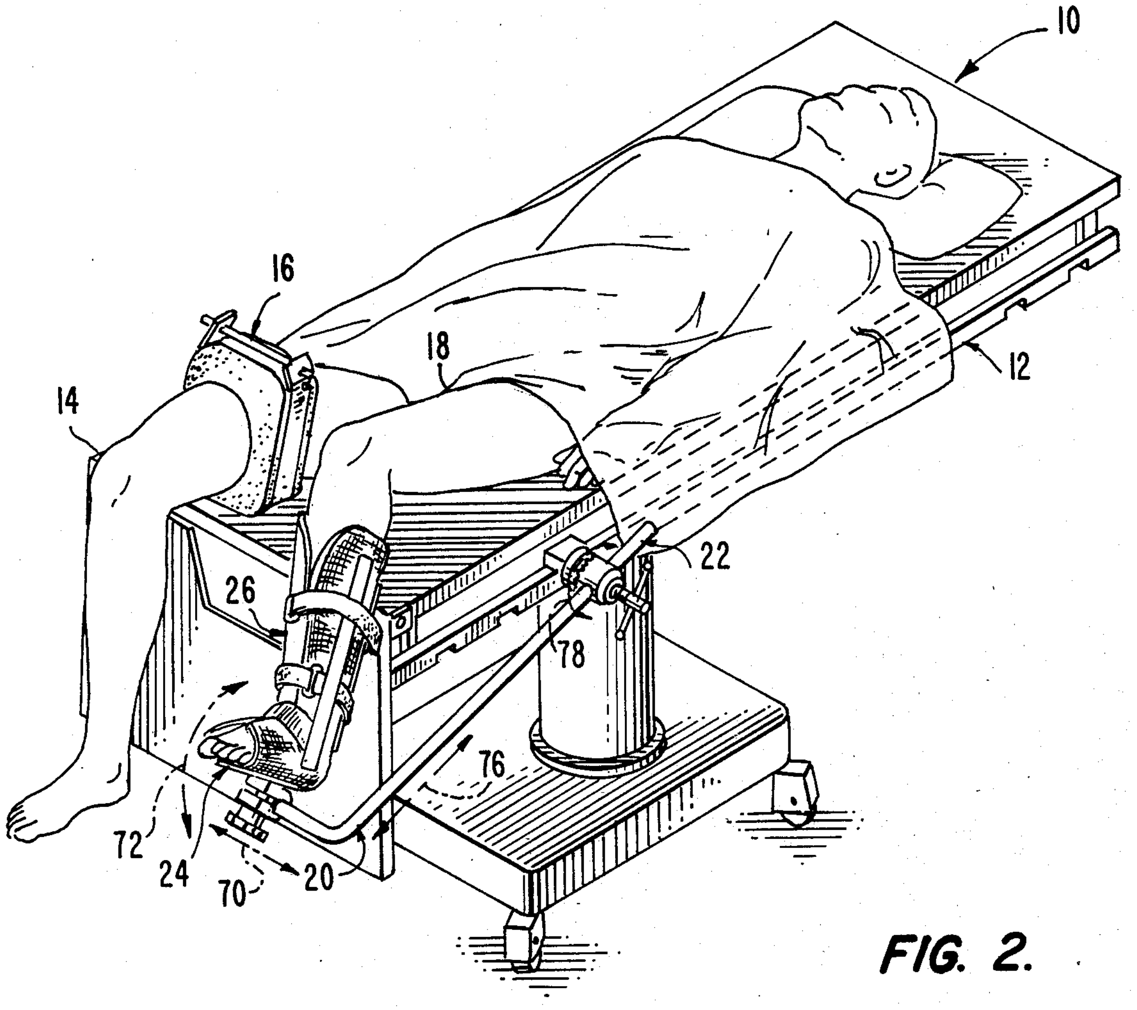
FIG. 1 is an axonometric, context of the invention, viewed disclosing a patient lying upon an operating table with an operative right leg secured by a circumferential collar about the thigh and a well leg raised and abducted in accordance with a preferred embodiment of the invention.

Referring now to the drawings, wherein like numerals indicate like parts, and initially to FIG. 1, there will be seen an operative context of the subject invention. More particularly, a patient 10 is shown laying in a reclined position upon an operating table with a an operative leg 14 positioned through an adjustable immobilizing collar 16 which is well known in the art. The patients non operative, or well leg 18 is shown in an elevated and abducted posture by use of a well leg operative support 20 in accordance with a preferred embodiment of the invention.

This well leg support 20 includes a generally L-shaped bar 22, an L-shaped foot bracket 24 and a flexible, disposable boot 26 which releasably enrobes the distal end of a patient's well leg. Through utilization of the subject well leg operative support, it will be noted that the patient's thigh is elevated approximately 45° or so and the leg is abducted to a non-interfering, yet secure, position with respect to the leg of operating interest 14.

Figure 2:
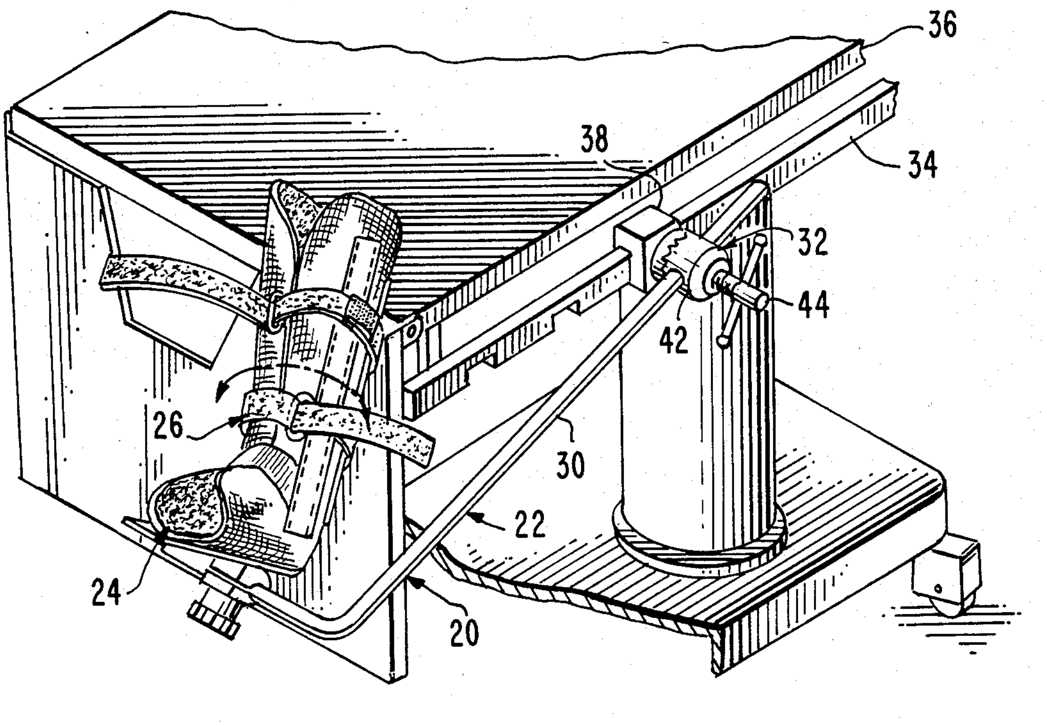
FIG. 2 is a detailed axonometric view of a well leg operative support in accordance with subject invention.

FIG. 2 is a more detailed, and unencumbered, view of the subject well leg operative support 20. The L-shaped bar 22 comprises a first leg 30 which is received for axial translation through a conventional Clark-type clamp 32 which is mounted upon a rail 34 of an operating table 36. The Clark-type clamp 32 is of a conventional design and is found on most operating tables and includes a generally U-shaped bracket 38 which is operable to be translated along rail 34 and in addition comprises a serated engagement portion which may be axially rotated with respect to the clamp 38. An aperture 42 extends transversely through the clamp 32 and a clockwise actuation of rod 44 is operable to fix the C-shaped clamp 38 upon rail 34, rotationally set the serations 40 and bind a rod in an axial position within bore 42.

Figure 3:
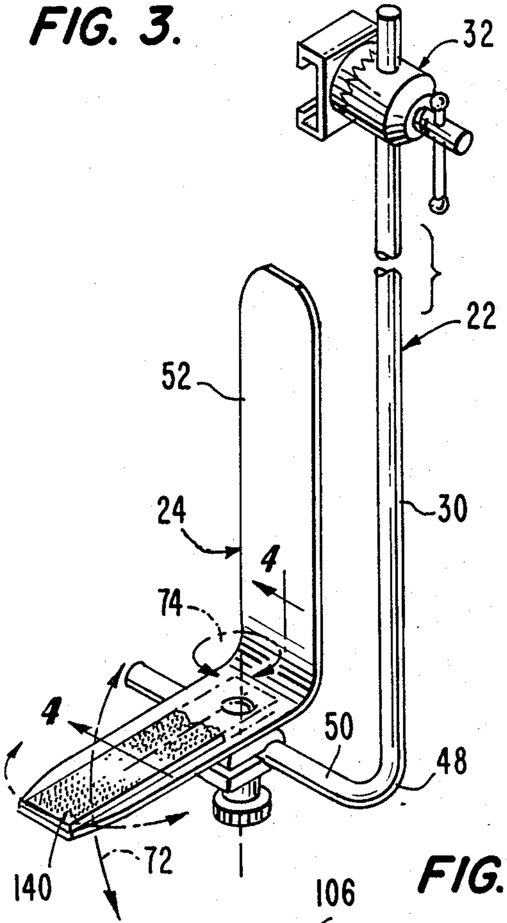
FIG. 3 is an axonometric detailed view of a detailed portion of a generally L-shaped support bar and L-shaped foot bracket supported upon a short leg of the L-shaped bar.
Figure 4:
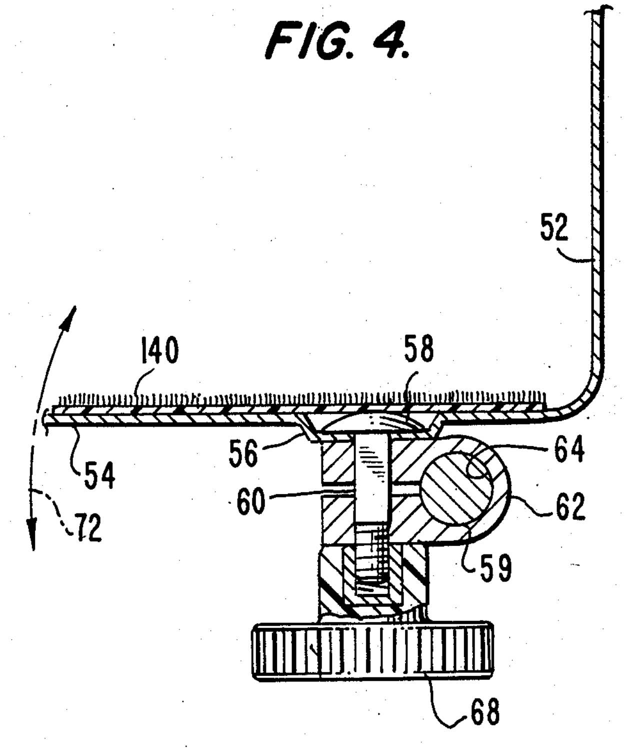
FIG. 4 is a cross-sectional detailed view of a segment of the L-shaped foot bracket as taken along section line 4—4 in FIG. 3.

Referring particularly to FIG. 3, the generally L-shaped bar 22 having a first leg 30 includes a generally 90° bend as at 48 and a second leg 50 which is axially shorter than the first leg 30. The second leg 70 operably extends beneath a generally L-shaped foot bracket 24 as previously noted in FIG. 2. The L-shaped foot bracket includes a generally elongate first panel 52 and a shorter sole panel 54 mounted at a right angle with respect to the back panel 52. As noted particularly in FIG. 4, the foot panel 54 is adjustably mounted transversely upon the short leg 50 of the generally L-shaped bar 22. In this connection, the foot panel 24 is fashioned with a recess 56 which operably receives the head 58 of a bolt 60. The shank of bolt 60 extends through a U-clamp 62 having a transverse bore 64 which is a dimensioned to intimately yet slidably translate along short leg 50 of the L-shaped bracket 22. An adjusting nut 68 releasably tightens the arms of the C-clamp 62 to permit clamping or frictional engagement of the clamp with respect to the short leg 50. As noted in FIGS. 3 and 4, the subject L-shaped foot bracket is adjustably mounted upon the short leg 50 with a first degree of adjustment in translation as noted by directional arrows 70, note again FIG. 1, pivotal adjustment as depicted by directional arrows 72 in FIGS. 1 and 5; and rotational adjustment as depicted by directional arrows 74 in FIG. 3. Accordingly, the L-shaped bracket is provided with 3 degrees of adjustment with respect to an underlying transverse leg 50 of the L-shaped bar. The L-shaped bar in turn is provided with a first degree of translation adjustment as depicted by directional arrows 76 in FIG. 1 and rotational adjustment shown by directional arrows 78 via the Clark-type clamp connected to the side rail 34 of an operating room table.

Through manipulation of the above discussed adjustment members, a patient's well leg 18 may be elevated and abducted outwardly and then retained in a secured position at a desired degree such as a 45° elevation and 45° abduction or the like.

The subject well leg operative support further includes a flexible and disposable boot 26 as illustrated in detail in FIGS. 5–8. More specifically, the boot is preferably fashioned from a flexible cloth material having upstanding sidewalls 82 and 84 and an axial slit 86 extending along a front portion of the boot. The flexible walls 82 and 84 terminate in a foot portion 88 which in combination with the side walls are operable to enrobe the distal end of a patient's well leg.

The boot is preferably lined with a synthetic wool like material 90 and is comfortably yet securely retained about a patient's lower leg by an instep strap 92 and a first 94 and second 96 circumferential leg strap. Each of the retaining straps of the boot is fashioned from a material having a flexible backing 98 and a plurality of loops fashioned upon one surface 100. Loops of the type envisioned by the subject invention form one part of a hook and loop type connection combination sold under the trademark of Velcro and operably cooperate with hook portions performed on a connection backing member. In this connection and with specific reference to FIG. 5, a hook patch 100 is connected to the sidewall boot 26 and operably receives and retains adjustable connection with the strap 98 through mild pressure application as indicated by directional arrow 104 in FIG. 5.

Figure 5:
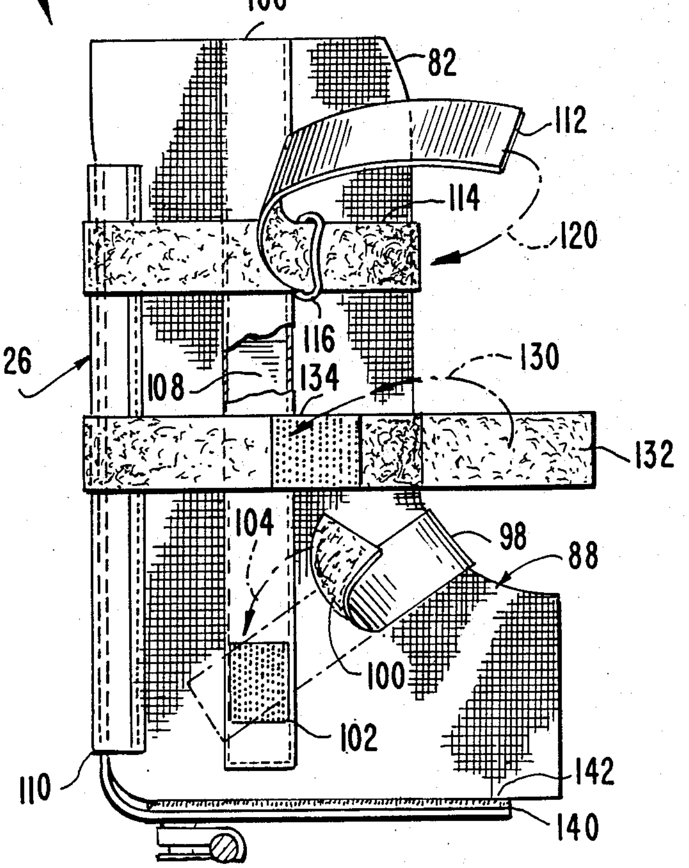
FIG. 5 is a side elevational view of a flexible, disposable boot operable to receive a patient's well leg in accordance with the subject invention.
Figure 6:
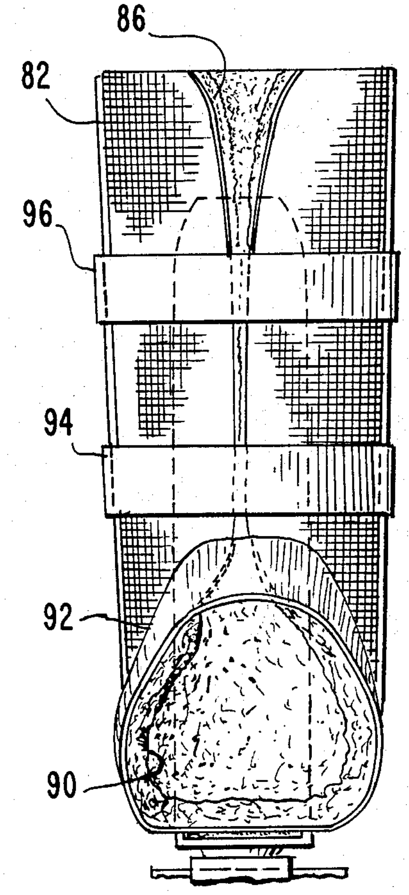
FIG. 6 is a front detailed view of the flexible boot disclosed in FIG. 5.

Referring in more detail to FIG. 5, the boot is fashioned with a laterally extending pocket 106 along each sidewall 82 and 84 and receives an internal stiffening member or stay 108 which is preferably composed of a rather stiff metal strip.

Figure 7:
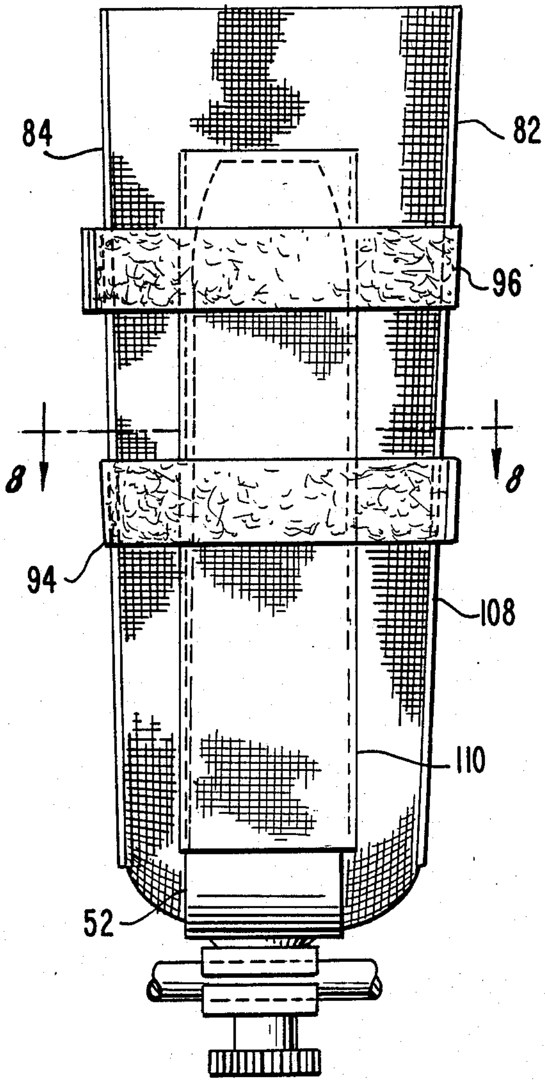
FIG. 7 is a back view of the subject flexible boot including a longitudinally extending rear pocket operable to receive in telescopic engagement a long upright leg of the L-shaped foot bracket disclosed in FIG. 3.
Figure 8:
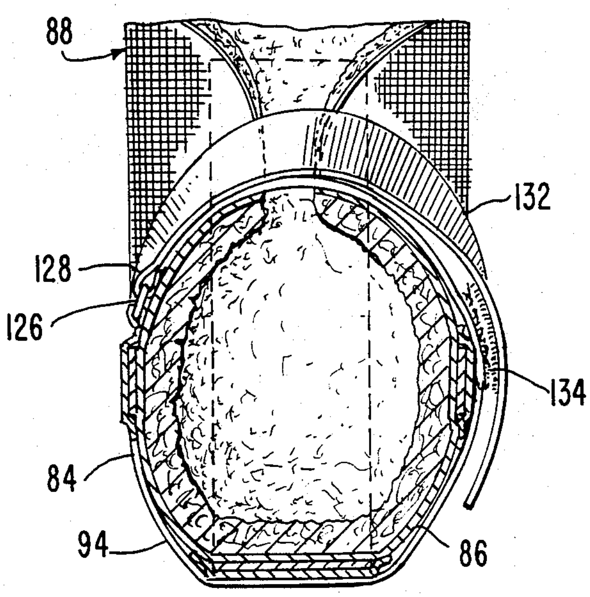
FIG. 8 is a broken away detailed view of the subject flexible boot as taken along section line in FIG. 7.

In addition, the boot is fashioned with a longitudinally extending back panel 110, note particularly FIGS. 5 and 7 which operably receives the long leg 52 of the L-shaped foot bracket 24.

The circumferential leg bands 94 and 96 operably extend about the leg portion of the flexible boot and with specific reference to FIG. 5, the lateral strap 96 is fashioned from a flexible backing 112 and a loop material 114. A generally rectangular retaining ring 116 is mounted adjacent to a lateral pocket 106 and the strap extends across the internal stiffening member 108 and around circumferentially around the boot and across slit 96. A free end of the strap 96 is extended through the generally rectangular bracket 116 and is reversibly returned as indicated by directional arrow 120 in FIG. 5. A generally rectangular hook patch, not shown, but similar to patch 102 having hooks on both sides is connected to an outside portion of strap 96 and operably receives the free end of the reversely returned strap to retain the lateral strap 96 circumferentially about, and closing the slit 86 with respect to the leg of a patient.

Further in the above connection a lower strap 94 is shown wherein a generally rectangular ring 126 is mounted upon an opposite lateral portion of the flexible boot and the strap 94 is looped through the bracket 126 as at 128 and is reversely returned as indicated by directional arrow 130, note FIG. 5. A free end 132 of the strap 94 is retained in position by an inside loop surface of the strap being releasably secured to a double sided hook patch 134 as specifically shown in FIGS. 5 and 8.

As particularly shown in FIG. 3, the sole portion of the L-shaped foot bracket operatively receives a generally rectangular strip of hook or loop member 140 of a Velcro combination and a base or lower foot portion of the boot is fitted with a corresponding generally rectangular patch 142 of loop or hook material to cooperate with the member 140 and releasably retain a bottom portion of the boot securely on the foot support bracket 24 as illustrated particularly in FIG. 5.

In use, a patient to receive surgery is prepared in a pre-operative environment such as the patient's room by being comfortably fitted, while the patient is awake, with the subject well leg, flexible boot 26.

The patient is then sedated and brought into an operating theater and placed upon an operating table wherein an orderly and/or nurse operably telescope the back portion 52 of the L-shaped foot bracket 24 into the longitudinally extending pocket 112 of the flexible boot. When the sole of the patient's well leg reaches the base 54 of the L-shaped bracket, the matching hook and loop patches cooperate under mild pressure to releasably secure the boot 26 with respect to the bracket 24.

A nurse and/or physician may then axially adjust the long leg 30 of the L-shaped bar 22 within a Clark type clamp to a desired translation and rotational position for the size of a particular patient. In addition, the clamping nut 68 is released and the L-shaped foot bracket is permitted to be laterally translated along the underlying short leg 50 of the L-shaped bar 22. In addition, the L-shaped foot bracket 24 is adjustably rotated as indicated by directional arrows 72 and 74 with two degrees of freedom such that a patient's well leg 18 is securely elevated and abducted out of interfering location with respect to an operative knee 14 without damaging the well leg.

SUMMARY OF MAJOR ADVANTAGES OF THE INVENTION

After reading and understanding the foregoing inventive well leg operative support, in conjunction with the drawings, it will be appreciated that several distinct advantages of the subject invention are obtained.

Without attempting to set forth all of the desirable features of the instant well leg operative support, at least some of the major advantages of the invention include the unique combination of a generally L-shaped bar 22 having a short leg 50 which operably extends beneath the base of a generally L-shaped foot bracket 26 and securely prevents the bracket from ever "falling off" the L-shaped bar during adjustment.

A flexible, and disposable boot 26 is operably positioned upon the L-shaped bracket 34 in an operating room and in accordance with the subject structure may be utilized to facilely yet securely elevate and abduct a patient's well leg during an arthroscopic and/or incision operative procedure upon a patients other leg.

The flexible sidewalls and 82 and 84 of the disposable boot receive axially extending stiffening stays 108 which cooperate with an instep 92 and pair of circumferential leg bands 94 and 96 to form a substantially rigid retaining member about the distal end of the patient's well leg.

A back pocket 110 of the flexible boot 26 permits the boot to be applied to a patient in the patient's room upon the well leg and upon entering an operating room, the boot is then releasably connected to the L-shaped bracket by sliding the long leg 52 of the bracket into the pocket 110 releasably securing the boot by the provision of cooperating hook and loop patches upon the sole of the boot and top portion of the L-shaped bracket.

The provision of at least two independent leg straps and an instep strap permits a surgeon to adjustably secure the boot with respect to patients having a range of human size without necessitating the manufacture of a variety of sized parts. Moreover, the flexible boot is relatively inexpensive and disposable following an operative procedure.

The combination of a bolt 60 and C bracket 62 which is mounted upon the short leg 50 of the L-shaped foot bracket 24 enables a physician to advantageously manipulate and adjust the well leg support structure to elevate and abduct a patient's well leg to a desired degree with a minimum of effort and a maximum amount o security.

The provision of the lateral straps 94 and 96 of the flexible boot, which extend in opposite directions and utilized generally rectangular loop patches which receive the straps with a reverse direction enables secure yet adjustable application of the flexible boot about a patient's leg in a patient's room and within operating theater.

In describing the invention, reference has been made to a preferred embodiment and illustrative advantages of the invention. Those skilled in the art, however, and familiar with the instant disclosure of the subject invention, may recognize additions, deletions, modifications, substitutions and other changes which will fall within the purview of the subject invention and claims.

What is claimed is:

1. A well leg operative support for use during an arthroscopic and/or incision surgical procedure comprising:

a generally L-shaped bar having, a first leg, and a second leg wherein said first leg is longer than said second leg and said first leg is operative to be securely retained by a clamp connected to an operating table;

a generally L-shaped foot bracket adjustably connected to said second leg of said generally L-shaped bar;

a disposable boot operable to embrace the foot of a patient's well leg and releasably secure the foot to said L-shaped foot bracket, said disposable boot including a foot portion, a lower leg engaging portion, at least one essentially rigid lateral splint member axially extending, in a pocket along said lower leg engaging portion to laterally stabilize said disposable boot wherein a patient's foot of a well leg may be operably secured to said L-shaped foot bracket and said L-shaped bar is axially adjusted within a clamp connected to an operating room table and said L-shaped foot bracket is rotationally and laterally adjusted with respect to said second leg of said L-shaped bar to flex a patient's well leg hip and knee and abduct the well leg prior to an orthopedic examination and/or surgical procedure, said boot further comprising a longitudinally extending pocket fashioned along a back portion of said disposable boot and being operable to receive a long leg of said L-shaped foot bracket to releasably secure said disposable boot to said generally L-shaped foot bracket.

2. A well leg operative support as defined in claim 1 wherein said disposable boot comprises:

a flexible cloth member having an axial slit generally along a front portion thereof to facilitate placement of the foot of a patient's well leg within said disposable boot; and at least one releasable retaining means for securing said flexible cloth member about a lower leg and foot portion of a patient's well leg.

3. A well leg operative support as defined in claim 2 wherein said releasable retaining means comprises:

at least one arch strap positioned across an instep portion of said disposable boot; and at least one leg strap positioned around a leg portion of said disposable boot.

4. A well leg operative support as defined in claim 3 wherein said releasable retaining means comprises:

at least two independent leg straps axially spaced along the leg portion of said boot and each circumferentially encompassing said leg position.

5. A well leg operative support as defined in claim 4 wherein each of said independent leg straps comprises:

a generally rectangular ring secured at one end of said strap and adhered to a lateral wall surface of said leg portion of said disposable boot and said strap operably extending circumferentially about said leg portion of said disposable boot through said ring and reversely returned and secured to form a circumferential band about said leg portion of said disposable boot.

6. A well leg operative support as defined in claim 5 wherein:

each of said independent leg straps includes a flexible backing on one side and loop material on the other side; and a double sided hook patch releasably retained between loop portions of said reversely returned portion of said independent leg strap

7. A well leg operative support as defined in claim 1 wherein:

said disposable boot includes one of a loop strip and a hook strip on a bottom area of said foot portion; and said generally L-shaped foot bracket includes the other of said loop strip and hook strip on a top area of a short leg of said L-shaped foot bracket such that said disposable boot may be releasably secured to the short leg of said L-shaped foot bracket by engagement of said hook strip with said loop strip.

8. A well leg operative support as defined in claim 1 wherein said at least one lateral splint member comprises:

a first essentially rigid stay member;

a second essentially rigid stay member; and said disposable boot is composed of a flexible material and having a longitudinally extending pocket laterally fashioned within opposing sides of the lower leg engaging portion of said disposable boot and being operable to receive said first and second essentially rigid stay members to laterally stabilize said disposable boot.

9. A well leg operative support as defined in claim 1 wherein:

said generally L-shaped foot bracket is adjustably connected to said second leg of said generally L-shaped bar extending beneath said generally L-shaped foot bracket with one degree of adjustment in translation and at least one degree of adjustment in rotation.

10. A well leg operative support as defined in claim 9 wherein:

said at least one degree of rotational adjustment comprises two degrees of rotational adjustment of said L-shaped foot bracket with respect to said underlying second leg of said generally L-shaped bar.

11. A well leg operative support for use during an arthroscopic and/or incision surgical procedure comprising:

a generally L-shaped bar having a first leg, and a second leg wherein said first leg is longer than said second leg and said first leg is operative to be securely retained by a clamp connected to an operating table;

a generally L-shaped foot bracket adjustably connected to said second leg of said generally L-shaped bar wherein said second leg operably extends beneath said L-shaped foot bracket;

a disposable boot operable to embrace the foot of a patient's well leg and releasably secure the foot to said L-shaped foot bracket, said disposable boot including, a flexible cloth member having an axial slit generally along a front portion thereof to facilitate placement of the foot of a patient's well leg within said disposable boot;

said boot including a foot portion and a lower leg embracing portion;

at least one essentially rigid lateral splint member axially extending along said lower leg engaging portion to laterally stabilize said flexible cloth, disposable boot;

at least one releasable retaining means for securing said flexible cloth member about a lower leg and foot of a patient's well leg; and a longitudinally extending pocket fashioned upon a back segment of said lower leg engaging portion of said disposable boot and being operable to receive a long leg of said L-shaped foot bracket to releasably secure said disposable boot to said generally L-shaped foot bracket, wherein a patient's foot of a well leg may be operably secured to said L-shaped foot bracket and said L-shaped bar is axially adjusted within a clamp connected to an operating room table and said L-shaped foot bracket is rotationally and laterally adjusted with respect to said second leg of said L-shaped bar to flex the hip and knee of a patient and abduct the well leg prior to an orthopedic examination and/or surgical procedure.

12. A well leg operative support as defined in claim 11 wherein:

said at least one lateral splint member comprises, a first essentially rigid stay member, and a second essentially rigid stay member; and said disposable boot includes longitudinally extending lateral pockets fashioned upon opposing sides of the lower leg engaging portion of said disposable boot and being operable to receive said first and second essentially rigid stay members to laterally stabilize said disposable boot.

13. A well leg operative support as defined in claim 12 wherein said releasable retaining means comprises:

at least one arch strap positioned across an instep portion of said disposable boot; and at least one leg strap positioned around a leg portion of said disposable boot.

14. A well leg operative support as defined in claim 13 wherein said releasable retaining means comprises:

at least two independent leg strap axially spaced along the leg portion of said boot and each circumferentially encompassing said leg portion and said lateral splints.

15. A well leg operative support as defined in claim 14 wherein each of said independent leg straps comprises:

a ring secured at one end of said strap and connected to a lateral wall surface of said leg portion of said disposable boot at a location adjacent to one of said lateral splints and said strap operably extending circumferentially about said leg portion of said disposable boot through said ring and reversely returned and secured to form a circumferential band about the leg portion of said disposable boot; each independent leg strap being composed of a flexible backing on one side and loop material on the other side and a double sided hook pad is releasably retained between opposing loop portions of said reversely returned portion of said independent leg strap.

16. A well leg operative support comprising:

a generally L-shaped bar having a first leg, and a second leg wherein said first leg is longer than second leg and said first leg is operative to be securely retained by a clamp connected to an operating table;

a generally L-shaped foot bracket adjustably connected to said second leg of said generally L-shaped bar, said generally L-shaped foot bracket being adjustably connected to said second leg of said generally L-shaped bar extending beneath said generally L-shaped foot bracket with one degree of adjustment in translation and at least one degree of adjustment in rotation;

a disposable boot operable to embrace the foot of a patient's well leg and releasably secure the foot to said L-shaped foot bracket, said disposable boot including, a foot portion, a lower leg engaging portion;

said disposable boot being composed of a flexible cloth member having an axial slit generally along a front portion thereof to facilitate placement of a foot of a patient's well leg within said disposable boot, at least one releasable retaining means for securing said flexible cloth member about a lower leg and foot of a patient's well leg, and at least one essentially rigid lateral splint member axially extending along said lower leg engaging portion to laterally stabilize said disposable boot wherein a patient's foot of a well leg may be operably secured to said L-shaped foot bracket and said L-shaped bar is axially adjusted within a clamp connected to an operating room table and said L-shaped foot bracket is rotationally and laterally adjusted with respect to said second leg of said L-shaped bar to flex the hip and knee of a patient and abduct the well leg prior to an operative examination and/or surgical procedure said boot further comprising a longitudinally extending pocket fashioned upon a back portion of said lower leg engaging portion of said disposable boot and being operable to receive a long leg of said L-shaped foot bracket to releasably secure said disposable boot to said generally L-shaped foot bracket.

17. A well leg operative support as defined in claim 16 wherein:

said at least one degree of rotational adjustment comprises two degrees of rotational adjustment of said L-shaped foot bracket with respect to said underlying second leg of said generally L-shaped bar.

18. A well leg operative support as defined in claim 17 wherein said disposable boot further includes, a first essentially rigid stay member;

a second essentially rigid stay member; and said disposable boot further being fashioned with a longitudinally extending lateral pocket upon opposing sides of the lower leg portion of said disposable boot and being operable to receive said first and second essentially rigid stay members to laterally stabilize said disposable boot.

19. A well leg operative support as defined in claim 18 wherein said releasable retaining means comprises:

at least one arch strap positioned across an in-step portion of said disposable boot; and at least one leg strap positioned around a leg portion of said disposable boot.

* * * * *